United States Patent [19]

Nardella

[11] Patent Number: 5,207,691

[45] Date of Patent: May 4, 1993

[54] ELECTROSURGICAL CLIP APPLICATOR

[75] Inventor: Paul C. Nardella, North Easton, Mass.

[73] Assignee: Medical Scientific, Inc., Taunton, Mass.

[21] Appl. No.: 786,574

[22] Filed: Nov. 1, 1991

[51] Int. Cl.[5] .............................................. A61B 17/00
[52] U.S. Cl. ..................................... 606/142; 606/143; 606/27; 606/139; 606/41; 227/901; 128/783
[58] Field of Search ................... 606/143, 142, 51, 52, 606/139, 41, 34, 32; 128/785

[56] References Cited

U.S. PATENT DOCUMENTS

| 3,100,489 | 8/1963 | Bagley | 606/42 |
|---|---|---|---|
| 3,270,745 | 9/1966 | Wood | 606/207 |
| 3,775,825 | 12/1973 | Wood et al. | 606/142 X |
| 4,038,984 | 8/1977 | Sittner . | |
| 4,041,952 | 8/1977 | Morrison, Jr. et al. | 606/51 X |
| 4,114,623 | 9/1978 | Meinke et al. | 606/139 |
| 4,201,314 | 5/1980 | Samuels et al. | 606/151 X |
| 4,397,312 | 8/1983 | Molko | 606/207 |
| 4,503,855 | 3/1985 | Maslanka . | |
| 4,658,819 | 4/1987 | Harris et al. | 606/34 |
| 4,682,598 | 7/1987 | Beraha | 606/142 |
| 4,712,544 | 12/1987 | Ensslin . | |
| 4,712,549 | 12/1987 | Peters et al. | 606/143 |

Primary Examiner—Stephen C. Pellegrino
Assistant Examiner—Jeffrey A. Schmidt
Attorney, Agent, or Firm—Lahive & Cockfield

[57] ABSTRACT

A clip applicating device deploys surgical clips to ligate ducts and/or vessels during surgical procedures. While the clip is deployed the device simultaneously delivers electrosurgical energy to the affected tissue through the clip. This causes the clip and the adjacent tissue to be fused together, resulting in more secure surgical clips. The clipping device may be configured either as a bipolar or a monopolar instrument.

20 Claims, 4 Drawing Sheets

ELECTROSURGICAL CLIP APPLICATOR

BACKGROUND OF THE INVENTION

The invention relates to an electrosurgical device which delivers surgical clips to tissues such as ducts or vessels.

Ligation or occlusion of ducts, veins, arteries or blood vessels is common in many surgical procedures. Often it is desirable to do so using one or more surgical clips which are intended to remain in place on either a temporary or permanent basis. Many designs for surgical clips and clip applying devices are well known in the art.

Where surgical clips are intended to Permanently ligate a duct, vein, artery or vessel it is, of course, important that the clip not become dislodged or displaced over time. However, it is believed that approximately 30 percent of all permanently installed surgical clips do become dislodged or displaced over the course of time. Such dislodgement or displacement of the clip can result in the undesirable release of fluid or blood.

Accordingly, it would desirable to provide a surgical clip applying device which enables surgical clips to be installed more securely so that they are less prone to displacement or dislodgement.

It is thus an object of the invention to provide an electrosurgical surgical clip applying device which is able to install surgical clips safely and more securely. Another object is to provide a clip applying device which securely bonds a surgical clip to adjacent tissue which more securely introduces surgical clips to tissue. It is also an object to provide a surgical clip applying device which delivers clips in such a way that the clip is securely installed and clip-to-tissue fusion and tissue-to-tissue fusion are promoted. A further object is to provide a method of securely installing surgical clips during surgical procedures. Other objects will be apparent to those skilled in the art upon reading the disclosure which follows.

SUMMARY OF THE INVENTION

The present invention relates to an electrosurgical device for applying surgical clips to tissues such as ducts, veins, arteries, and blood vessels. The surgical clip applying device includes a handle portion which has a triggering mechanism which cooperates with an actuating mechanism for deploying surgical clips. Adjacent the handle portion is a member, which preferably is elongate, and which houses the mechanisms for actuating the deployment of surgical clips. The elongate member may also house a supply of surgical clips.

Further, electrosurgical energy is communicated from a source remote from the clip applicator device for delivery of electrical current through the clip to the tissue in contact with the clip. The electrical current delivered to the tissue through the clip is electrosurgical energy, preferably in the radio frequency range. The application of electrosurgical energy to tissue effects a fusing of tissue to the clip, as well as a fusing of tissue within the duct or vessel. Surgical clips which are electrosurgically applied in this manner are more secure, and are much less prone to becoming dislodged or displaced. Also, the tissue-to-tissue fusion minimizes the likelihood of an undesirable release of fluid or blood from the affected duct or vessel.

In one embodiment, the clip applying device is in the form of a monopolar instrument in which the individual clips serve as the active electrode, and a remote ground plate, in contact with a patient, serves as the return electrode.

Alternatively, the clip applying device may function as a bipolar electrosurgical instrument. In this embodiment the device would simultaneously deploy at least two clips which are electrically isolated from each other. A first clip serves as an active electrode which communicates electrical energy to the tissue, while the second clip serves as the return electrode.

DETAILED DESCRIPTION OF THE INVENTION

Figure 1:
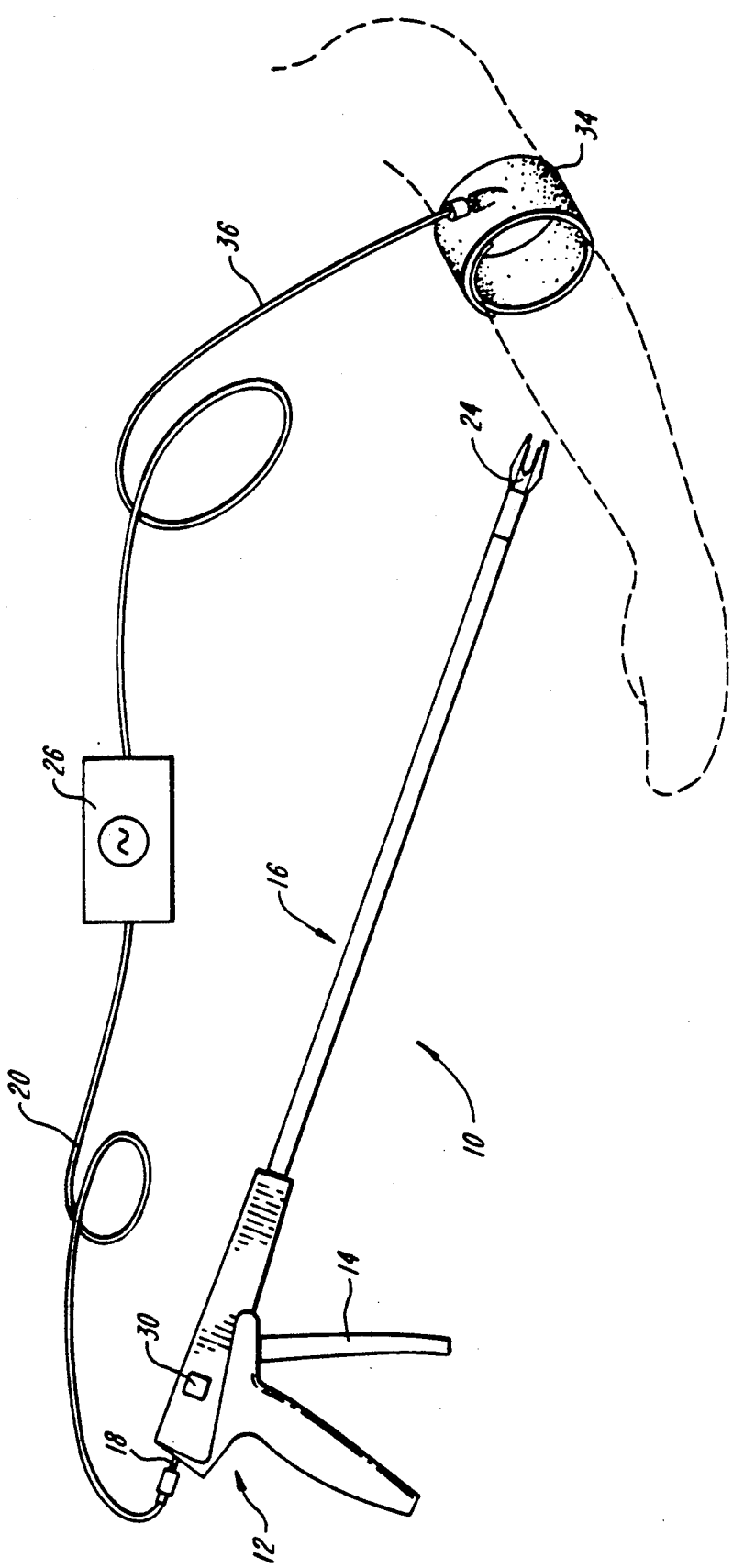
FIG. 1 is a schematic view of an electrosurgical clip applicating device according to the present invention.

FIG. 1 illustrates a representative surgical clip applicating device 10 with which the present invention is applicable.

The clip applicator 10 includes a handle portion 12 having a trigger mechanism 14. Adjacent the handle is an elongate member 16 which houses a supply of surgical clips (not shown) as well as an actuating mechanism, described below, which assists in deploying the clips. The handle 12 also includes an electrical connector port 18 which is able to be connected to insulated wire 20 which communicates electrosurgical energy from generator 26.

Figure 2:
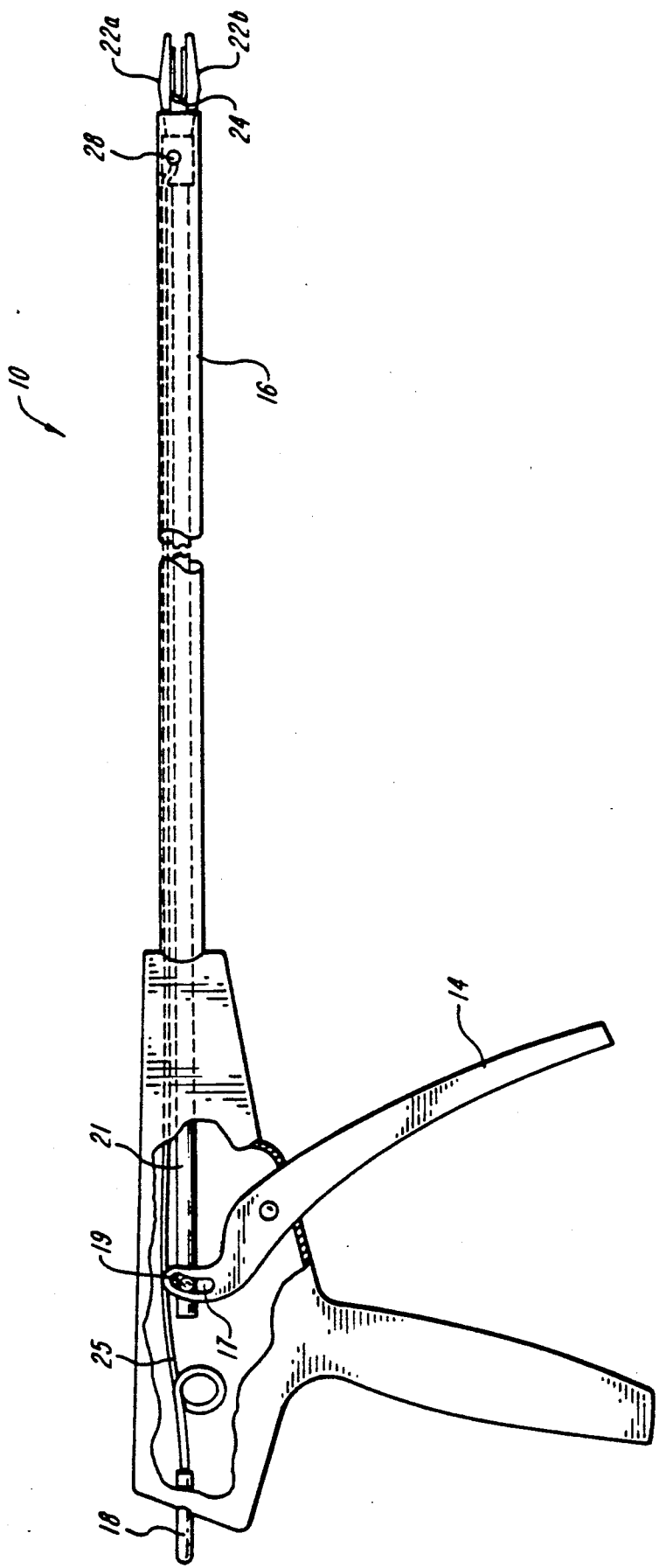
FIG. 2 is a side, partially cut-a-way view of the electrosurgical clip applicating device of FIG. 1.

An actuating mechanism adaptable for use with the present invention is illustrate in FIG. 2. The actuating mechanism preferably includes an actuating rod 21 which communicates with the trigger mechanism 14 through a catch 19 which mounts within groove 17 of trigger 14. Actuating rod 21 also communicates with paired clamping jaws 22a, 22b which extend from a distal end of barrel 16. The clamping jaws 22a, 22b are adapted to engage and deploy a surgical clip 24. Surgical clips can be deployed by activation of the trigger mechanism 14, causing actuating rod 21 to move backwards (toward the handle 12) while closing clamping jaws 22a, 22b together. When the clamping jaws 22a, 22b are closed, the surgical clip 24 disposed between the jaws is clamped about a duct or vessel. Once a clip is deployed, a new clip may be positioned between clamping jaws 22a, 22b either automatically or manually.

Electrosurgical generator 26 communicates with clipping device 10 through external conductive wire 20 which connects to the clipping device through port 18. As shown in FIG. 2, port 18 communicates with internal conductor wire 25 which extends into the clipping device 10. Preferably, internal wire 25 is attached to a conductive portion of the actuating mechanism which is in electrical communication with surgical clip 24 to be deployed. The embodiment illustrated in FIG. 2 is configured such that the wire 25 terminates in a connection point 28 at the base of clamping jaws 22a, 22b. In an alternative embodiment (not illustrated) wire 25 may attach to actuating rod 21 which is made from a conductive material and which is in electrical communication with clamping jaws 22a, 22b. The portions of the clipping device 10 which are in electrical communication with wire 20 (e.g., actuating rod 21 and/or clamping jaws 22a, 22b) preferably are electrically isolated from the remainder of the tool.

Upon activating the delivery of current to tool 10, for example by activating switch 30, current will be delivered through internal wire 25 and communicated to surgical clip 24 through actuating rod 21 and/or clamping jaws 22a, 22b.

FIG. 1 further illustrates the configuration of the clip applicating device 10 when used as a monopolar instrument. This embodiment utilizes a ground element 34 which is remote from the device 10, and placed in contact with a patient's body. The ground element 34 serves as a return electrode and communicates with generator 26 through conductive wire 36. In such a configuration the clip 24 serves as the active electrode which delivers electrosurgical energy to tissue which it contacts.

Figure 3:
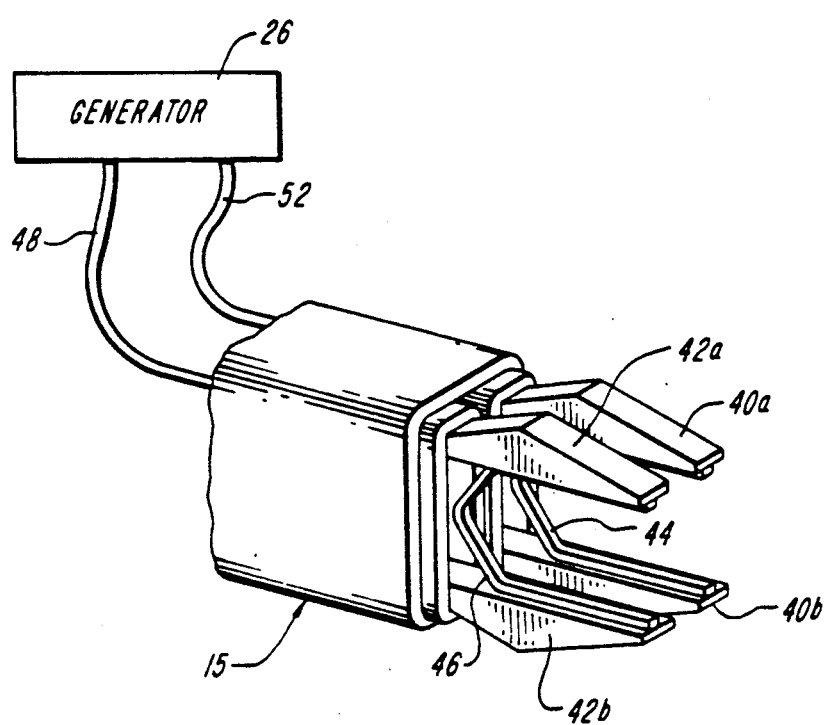
FIG. 3 is a schematic view showing a forward, clip deploying portion of an electrosurgical clip applicating device used in a bipolar mode.

FIG. 3 illustrates an embodiment of the invention in which the clip applicating device is configured as a bipolar electrosurgical instrument. Reference numeral 15 represents a forward portion of the barrel 16 which is adapted to receive dual pairs of clamping jaws 40a, 40b and 42a, 42b. The clamping jaws 40a, 40b and 42a, 42b each communicate with their respective actuating mechanism (not shown) which are electrically isolated from each other. Surgical clips 44 and 46 are shown positioned within jaws 40a, 40b and 42a, 42b.

In the bipolar embodiment insulated wire 48 communicates electrosurgical energy from generator 26 to clamping jaws 42a, 42b (or to the actuating mechanism associated with clamping jaws 42a, 42b). Wire 52 serves as a ground wire which communicates between jaws 40a, 40b (or the actuating mechanism associated with jaws 40a, 40b). Upon activation of a trigger mechanism jaws 40a, 40b and 42a, 42b close together to deploy clips 44 and 46. At the same time a control switch is activated to deliver electrical current to the actuating mechanism associated with jaws 42a, 42b and/or directly to jaws 42a, 42b, and hence to clip 46. When the clip contacts tissue, current is conveyed to the tissue causing the tissue and clip to be fused together. The electrosurgical energy also promotes tissue-to-tissue fusion. The applied current is returned to generator 26 through clamping jaws 40a, 40b, the actuating mechanism associated with these jaws, and wire 52.

Generator 26 supplies electrosurgical energy to the clipping device 10 in the manner described above. Virtually any generator able to provide electrosurgical energy for medical applications may be used with the present invention. Preferably, the generator is a voltage determinative, low source impedance generator which provides radio frequency energy. Preferably, a suitable generator can supply up to 2 amps of current and has an impedance value of less than 10 ohms.

The energy supplied by the generator to the clipping device is preferably in the radio frequency (RF) range. Although virtually any frequency in the RF range may be supplied to the clipping device, the preferred range is about 500 to 700 KHz, and most preferably about 550 KHz.

The energy requirements of the clipping device are dynamic and will vary depending upon the impedance values of tissue into which the clips are inserted. The impedance of tissue varies among tissue types and the amount of blood present in or around the tissue. The amount of current delivered by the tool to the tissue depends on the impedance of the tissue. Where the tissue contacted has a lower impedance value, more current will be delivered to the tissue through the clip, and, conversely, less current will be delivered where the tissue has a higher impedance value. Generally, the amount of current delivered ranges between 0.5 and 2.0 amps. The voltage applied to the tissue between the clip serving as the active electrode and the return electrode or ground plate is between about 50 and 100 volts RMS.

Figure 4A:
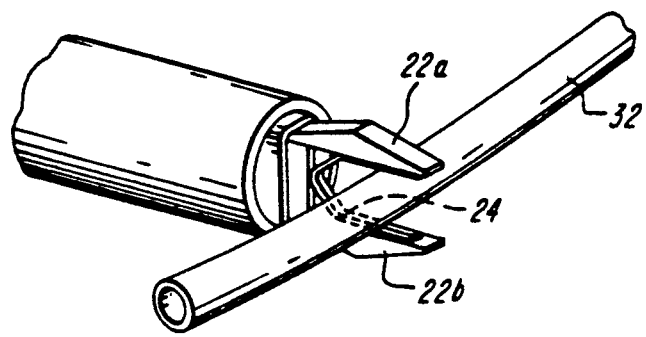
FIGS. 4A through 4C schematically illustrate the sequence in which a surgical clip is applied according to the present invention.
Figure 4B:
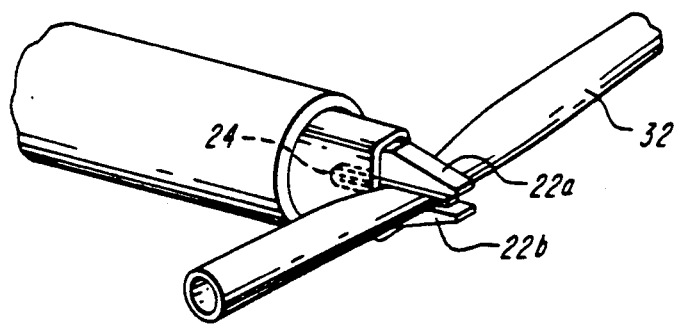
Figure 4C:
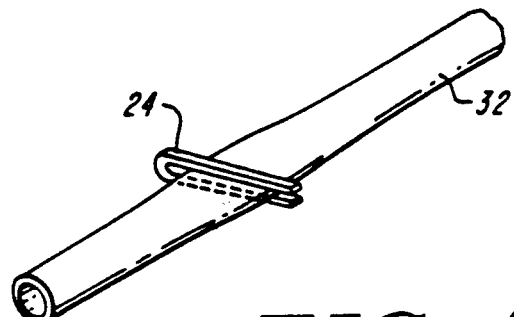

FIGS. 4A, 4B and 4C illustrate the manner in which surgical clips are deployed in accordance with the present invention. A vessel 32 to be ligated is disposed between clamping jaws 22a, 22b and surgical clip 24. Upon activating the triggering mechanism, the clamping jaws move together as shown in FIG. 4B, causing surgical clip 24 to close upon vessel 32. When the triggering action is completed the clip 24 remains adhered to the vessel 32 as illustrated in FIG. 4C. While the clip is applied over the vessel, electrosurgical energy is delivered through the clip 24, acting as an active electrode. Current is maintained for a suitable period of time, usually 5 to 15 seconds, to enable tissue-to-clip and tissue-to-tissue fusion to occur. As illustrated in FIG. 1, a ground clamp 34 which communicates with the generator through wire 36, can serve as the return electrode when the surgical clip applicator functions as a monopolar surgical device.

The actuating mechanism of clip applicator 10 preferably is made of a conductive material which has a relatively high tensile strength. Exemplary materials include surgical grade stainless steel and aluminum. Clamping jaws 22a, 22b likewise are made of a surgically compatible, conductive material suitable to enable current to be communicated through the clamping jaws 22a, 22b to clip 24. The surgical clips 24 used with the clipping device of the invention may be with a variety of constructions and may be made of variety of conductive, surgically compatible materials which are well known in the art. As illustrated the surgical clip may be substantially U- or V-shaped, but various other shapes or constructions are possible as well.

The handle portion 12, trigger 14, and the barrel 16 are electrically isolated from the remainder of the device. Preferably, these components are made of, or are coated with, non-conductive materials such as suitable polymers.

It is to be understood that the scope of the present invention encompasses surgical clip applicating devices having constructions other than those specifically described herein. That is, neither the overall configuration of the device nor the specific arrangement of mechanisms for deploying clips is critical. The present invention is potentially applicable to any surgical clipping device in which electrosurgical energy is delivered through the surgical clip to tissue in contact with the clip.

What is claimed is:

1. An electrosurgical clipping device, comprising:
    a handle portion adjacent and connected to an elongate member, the handle portion having a triggering means for deploying at least one surgical clip;
    a means for housing a supply of surgical clips within the device;
    a surgical clip delivery means for deploying at least one clip from the device to desired tissue, the clip delivery means extending from a distal end of the elongate member;

actuating means for effecting the deployment of one or more surgical clips through the delivery means in response to activation of the triggering means, the actuating means connecting between the triggering means and the delivery means;

supply means associated with the clipping device for delivering electrical current through the clipping device from a source remote from the clipping device to the delivery means for discharge through a clip to tissue contacted by the clip; and control means for selectively activating and regulating the electrosurgical energy delivered through the energy supply means to the delivery means.

2. The device of claim 1 wherein the actuating means and the delivery means are made of conductive materials.

3. The device of claim 2 wherein the supply means is in electrical connection with the actuating means such that electrical current is conducted through the actuating means to the delivery means.

4. The device of claim 3 wherein the supply means comprises an insulated electrical wire which extends from a connection port disposed on the device to a connection point on the actuating means.

5. The device of claim 4 where the supply means is in electrical communication a voltage determinative, low source impedance generator unit which provides electrosurgical energy.

6. The device of claim 5 wherein the generator provides electrosurgical energy in the range of 500–700 KHz.

7. The device of claim 6 wherein the current delivered to tissue through the clip is in the range of 0.5 to 2.0 amps.

8. The device of claim 6 wherein the voltage delivered to tissue through the clip is in the range of 50 to 100 volts RMS.

9. The device of claim 3 wherein the delivery means comprises at least one pair of opposed clamping elements which extend from a distal end of the elongate member.

10. The device of claim 9 wherein the actuating means communicates with first and second pairs of opposed clamping elements which extend from a distal end of the elongate member, and each pair is adapted to engage and close separate surgical clips for simultaneous deployment of the clips.

11. The device of claim 10 wherein the first pair of opposed clamping elements is electrically isolated from the second pair of opposed clamping elements.

12. The device of claim 11 wherein the supply means communicates with the first pair of clamping elements for discharge of electrosurgical energy through a first surgical clip to tissue in contact with the first clip.

13. The device of claim 12 wherein the second pair of clamping elements serve as a return electrode and are in electrical communication with a ground wire.

14. The device of claim 1, adapted to function as a monopolar electrosurgical tool, wherein the surgical clip to be deployed, through electrical connection to the delivery means, serves as an active, energy-delivering electrode, and a remote ground plate serves as a return electrode.

15. A method of electrosurgically applying a surgical clip to tissue, comprising the steps of:

providing a clip applicator device adapted to deploy one or more surgical clips;

deploying one or more surgical clips to body tissue;

delivering electrosurgical energy to tissue contacted by the clip, simultaneous with the deployment of the clip, the energy being communicated to the tissue through the surgical clip.

16. The method of claim 15 wherein the electrosurgical energy is supplied to the applicator device from an electrosurgical generator unit.

17. The method of claim 16 wherein the generator unit provides electrosurgical energy in the range of 500–700 KHz.

18. The method of claim 15 wherein the current applied to tissue through the clip is in the range of 0.5 to 2.0 amps.

19. The method of claim 15 wherein the voltage applied to tissue through the clip is in the range of 50 to 100 volts RMS.

20. The method of claim 15 wherein the electrosurgical energy is supplied to tissue, through the clip, for a duration of about 5 to 15 seconds.

* * * * *